US005162502A

United States Patent [19]

Barbieri et al.

[11] Patent Number: 5,162,502

[45] Date of Patent: Nov. 10, 1992

[54] MODIFIED TRICHOKIRIN AND THEIR PREPARATION FOR USE IN CONJUGATES AS INHIBITORS OF PROTEIN SYNTHESIS

[75] Inventors: Luigi Barbieri, Bologna; Pierre Casellas, Montpellier; Fiorenzo Stirpe, Bologna, all of Italy

[73] Assignee: Sanofi, Paris, France

[21] Appl. No.: 714,870

[22] Filed: Jun. 13, 1991

Related U.S. Application Data

[62] Division of Ser. No. 73,264, Jul. 14, 1987, Pat. No. 5,037,960.

[30] Foreign Application Priority Data

Jul. 15, 1986 [FR] France ................................ 8610296

[51] Int. Cl.[5] ................................ C07K 15/00

[52] U.S. Cl. ................................ 530/370; 530/350; 530/402; 530/408; 530/409; 530/410; 530/411; 530/395

[58] Field of Search ................ 530/350, 402, 408–411, 530/395, 370

[56] References Cited

U.S. PATENT DOCUMENTS 4,985,541 1/1991 Maraganore et al. .............. 530/350

OTHER PUBLICATIONS

Olsnes et al., *Pharmac. Ther.* vol. 15, 1982, pp. 355–381.

Ma et al., *Chem. Abst.* vol. 104(3) #173074, 1985.

Yeung et al., *Chem. Abst* vol. 107(5) #33362a, 1987.

*Primary Examiner*—Garnette D. Draper

*Attorney, Agent, or Firm*—Bacon & Thomas

[57] ABSTRACT

The present invention relates to a novel glycoprotein, extracted from the seeds of *Trichosanthes kirilowii*, called: trichokirin, as well as to its modified derivatives containing a free or blocked SH group. It relates to a process for its preparation, to its use and to pharmaceutical compositions in which it is present.

5 Claims, No Drawings

MODIFIED TRICHOKIRIN AND THEIR PREPARATION FOR USE IN CONJUGATES AS INHIBITORS OF PROTEIN SYNTHESIS

This application is a division of application Ser. No. 07/073,264, filed Jul. 14, 1987, now U.S. Pat. No. 5,037,960.

BACKGROUND OF THE INVENTION

1. Field of he Invention

The present invention relates to a novel inhibitor of protein synthesis and also to methods for its isolation, its use and pharmaceutical compositions in which it is present.

2. Background Information

Proteins which inhibit protein synthesis in eucaryotic systems have been found in the seeds or other parts of a number of plants. Among these proteins, ricin, abrin and modecin inhibit protein synthesis in both cellular systems and acellular systems and are therefore highly toxic to animals. By contrast, other proteins, which are effective only on acellular systems, have a low or zero toxicity to animals, perhaps because they cannot enter the cells.

In general, these proteins irreversibly inactivate the ribosomal subunit 60 S, which is then incapable of reacting with the elongation factor 2. Consequently, they are of interest in the study of protein synthesis and it has also been proposed to use them for combating tumors.

A protein of this type will be denoted hereafter by the term "ribosome-inactivating protein" (RIP). The best-known RIP is ricin, which is obtained by extracting the seeds of the castor-oil plant. Another RIP, gelonin, has recently been described and a review on RIP's has been published in FEBS Letters, 1986, 195 (1,2), pages 1–8.

A protein extracted from the roots of *Trichosanthes kirilowii*—trichosanthin—has recently been described (Nature, 1986, 321, 477–478) whose sequence is homologous to a certain degree with the subunit A of ricin D.

It has now been found that a novel and exceptionally powerful RIP which is different from trichosanthin can be extracted from the seeds of *Trichosanthes kirilowii*. This novel RIP will hereafter be referred to as "trichokirin".

SUMMARY OF THE INVENTION

Thus, according to one of its features, the present invention relates to the novel RIP called trichokirin, which has the following characteristics:

it is a glycoprotein with a molecular weight of 28,000±3000 as determined by electrophoresis on polyacrylamide gel in the presence of SDS (sodium dodecyl sulfate);

it has an isoelectric point ≧9;

it has a content of neutral sugars of 1.1 to 1.5% by weight, including 0.3 to 1.2% of mannose;

it has the following amino acid composition, expressed as the number of residues per mol of protein ±20%:

| | | | | | | | |
|---|---|---|---|---|---|---|---|
| Lys: | 17.3; | His: | 1.1; | Arg: | 6.7; | Asx: | 22.8; |
| Thr: | 18.9; | Ser: | 23.5; | Glx: | 21.6; | Pro: | 8.0; |
| Gly: | 16.0; | Ala: | 21.1; | ½ Cys: | 1.9; | | |
| Val: | 12.5; | Met: | 3.05; | Ile: | 15.8; | Leu: | 24.3; |
| Tyr: | 12.1; | Phe: | 10.1; | Trp: | n.d. | | |

where Asx represents the aspartic acid and asparagine residues together, Glx represents the glutamic acid and glutamine residues together, ½ Cys is the cystein residue of the native protein under the form of cysteic acid determined during the analysis and n.d. means "not determined", the other amino acids being designated according to the IUPAC recommendations; and it has the following terminal amino sequence:

1 ... 10

Asp—Val—Ser—Phe—Ser—Leu—Ser—Gly—Gly—Gly—

16

Thr—Ala—Ser—Tyr—Glu—Lys

The amino acid composition was determined by heating the glycoprotein at 105° C. for 24 hours under nitrogen, in the presence of 6N hydrochloric acid, 1% phenol and 1% 2-mercaptoethanol. The amino acids were converted to derivatives with phenyl isothiocyanate (PITC) in an alkaline medium. The phenylthiohydantions (PTH) so obtained were analyzed by reversed-phase HPLC. The cysteic acid was determined after oxidation of the protein with performic acid (J. Biol. Chem. 1963, 238, 235–237).

The terminal amino sequence was determined on a microsequencer marketed by Applied Biosynthesis, starting from 5 nmol of protein solubilized in a 10% aqueous solution of acetic acid. The PTH of the amino acids are analyzed by reversed-phase HPLC.

All these results, compared with those published in the literature for trichosanthin, clearly indicate that trichokirin and trichosanthin are 2 totally different substances.

According to another feature, the present invention relates to a process for the preparation of trichokirin, which comprises extracting the ground seeds of *Trichosanthes kirilowii* with water in the presence of a buffer at pH 6.5–7.5, removing the insoluble material, fractionating the extract by chromatography on a weakly acidic ion exchange resin using a buffer solution containing 0.3–0.6M sodium chloride at a pH of 7.2–7.7 as the eluent, and isolating and purifying the fraction containing the inhibitor protein; the low-molecular products can be removed by dialysis of the extract.

For example, the seeds of *Trichosanthes kirilowii*, preferably decorticated beforehand, are ground and extracted with water containing an electrolyte, for example sodium chloride, and a buffer, for example a phosphate-based buffer, at a pH around neutrality. The insoluble materials are then removed, for example by centrifugation, and the low-molecular substances are removed from the solution by dialysis, for example against phosphate buffer. The dialyzed extract is then fractionated, for example by chromatography on a weakly acidic ion exchange resin such as carboxymethyl cellulose. When this resin is employed, elution can be carried out using a linear concentration gradient, for example a 0 to 0.3M aqueous solution of sodium chloride. Normally, 4 main peaks are eluted and the 4th peak, eluted by a solution with a sodium chloride concentration of 0.03 to 0.11M, contains the major part of the trichokirin.

The trichokirin can be purified by gel filtration, for example on a column of Sephadex (registered trademark).

Trichokirin can be coupled to haptomers via an appropriate coupling agent. Thus, for example, trichokirin can be coupled to an antibody via a disulfide bridge by conventional methods.

To do this, both the trichokirin and the haptomer can be reacted with a reagent which makes it possible to introduce a chain carrying a disulfide group.

Another subject of the invention consists of modified derivatives of trichokirin containing a free or blocked SH group, and more particularly an S-acetylmercaptosuccinoyl-trichokirin obtained by treating trichokirin with S-acetylmercaptosuccinic anhydride, and the corresponding mercaptosuccinoyl derivatives prepared by reacting hydroxylamine with the S-acetyl derivative. The method for the preparation of trichokirin modified in this way is the one commonly used for the preparation of activated products, especially activated proteins. Thus, the introduction of the S-acetylmercaptosuccinoyl group into an antibody is described in U.S. Pat. No. 4,340,535, the introduction of the S-acetylmercaptosuccinoyl group into the primary hydroxyl of an ionophore is described in European Patent Application 162,781 and the introduction of the S-acetylmercaptosuccinoyl group into the A chain of ricin is described in European Patent Application 169,111.

These modified trichokirins can be represented by the formula:

$$TK^{\circ}-(CO-\underset{\displaystyle CH_2COOH}{\underset{|}{CH}}-S-W)_n \quad (I)$$

in which TK° represents the radical of trichokirin, W represents hydrogen or the acetyl group and n can vary between 0.2 and 3, preferably between 0.4 and 1, preferably still n=0.7.

The trichokirin of the present invention inhibits protein syntheses in a lyzate of reticulocytes with an $ID_{50}$ of 1.5-4 ng/ml. The effect is very much less on whole cells, the $ID_{50}$ varying from 7 to more than 100 μg/ml according to the cell examined.

Table 1 shows the effect of trichokirin on a variety of cells, especially the $ID_{50}$ (in μg/ml and $M.10^{-7}$) for the inhibition of protein synthesis; this was determined by applying the method described in J. Biol. Chem. (1984) 259, p. 9359-9364.

TABLE 1

| Cell | $ID_{50}$ μg/ml | $M \cdot 10^{-7}$ |
|---|---|---|
| Human fibroblasts | 3.9 | 1.3 |
| TG cells | 7.5 | 2.5 |
| NB 100 cells (neuroblastoma) | 10.3 | 3.4 |
| JAR cells (choriocarcinoma) | 16.3 | 5.4 |
| HeLa cells | 45.0 | 15.0 |
| M 4039 (melanoma) | 9.9 | 3.3 |

The toxicity of trichokirin to animals was evaluated on Swiss female mice weighing 27-32 g. The trichokirin is administered intraperitoneally at doses ranging from 0.56 to 20 mg/kg of body weight (with a ratio of 2 between 2 doses) to groups of 6 animals per dose. The 50% lethal dose ($LD_{50}$) is calculated by the Spearman-Karber method as described by Finney (Statistical Methods in Biological Assay, p. 524-530). The $LD_{50}$ of trichokirin is 8.1 mg/kg ±20%.

DETAILED DESCRIPTION OF THE INVENTION

The examples which follow illustrate the invention without however limiting it.

EXAMPLE 1

Isolation of Trichokirin

A) Crude extract

Seeds of *Trichosanthes kirilowii* (1.2 kg) are ground in an Ultraturrax apparatus with 8 volumes of a 0.14M aqueous solution of sodium chloride containing 5 mM phosphate buffer, pH 7.5. Extraction is continued overnight at 4° C., with magnetic stirring.

After removal of the coarse residues, the extract is centrifuged at 10,000 g for 45 minutes at 0° C. The supernatant is decanted in the cold to remove the solidified fats, after which the proteins are precipitated by the addition of ammonium sulfate up to saturation point. After centrifugation as indicated above, the precipitated product is resuspended in 1 liter of a 0.14M aqueous solution of sodium chloride containing 5 mM phosphate buffer, pH 7.5. The undissolved product is removed by centrifugation under the same conditions as above. The supernatant is transferred to a column of Sephadex R G 25 coarse marketed by Pharmacia (95 cm×10 cm), equilibrated with 5 mM phosphate buffer, pH 7.0, at room temperature, and eluted at a rate of 3 l/hour. The first protein peak is collected; this is the crude extract.

B) Ion exchange chromatography

The combined crude extracts from 2 operations (originating from 2.4 kg of seeds) are treated with sodium chloride up to a final concentration of 30 mM and transferred to a column of CM-Sepharose R Fast Flow marketed by Pharmacia (17.5 cm×5 cm), equilibrated with 30 mM phosphate buffer, pH 7.0. After the column has been washed with the same buffer, the bound protein is eluted by a gradient containing from 30 to 110 mmol/l of sodium chloride in the same phosphate buffer (volume 20 liters). 400 ml fractions are collected at a rate of 1.2 liters per hour. The elution is followed by measuring the absorbance at 280 nm and the conductivity of the eluate. The fractions showing an inhibitory activity against protein synthesis are combined (3.6 l) and brought to pH 5.8 with acetic acid. The solution is transferred to a column of S-Sepharose Fast Flow (6.6 cm×5 cm), equilibrated with 10 mM sodium acetate buffer, pH 4.5. After the column has been washed with the same buffer, the fixed inhibitor protein is eluted with 20 mM phosphate buffer, pH 7.5, containing 0.5M sodium chloride.

The fraction corresponding to the peak containing the inhibitor protein (200 ml) is collected, dialyzed against 3 times 50 l of distilled water and then lyophilized to give 380 mg of crude trichokirin.

C) Gel filtration

The trichokirin obtained above is dissolved in 50 ml of a 0.14M aqueous solution of sodium chloride. An insoluble material is removed by centrifugation at 20,000 g for 30 minutes. The supernatant is transferred to a column of Sephadex G 50 coarse (95 cm×5 cm), equilibrated with 30 mM phosphate buffer, pH 7.0, at 4° C. Elution is carried out at a rate of 60 ml/hour. The fraction corresponding to the peak containing the protein is collected, dialyzed and lyophilized as indicated above.

This gives 267 mg of purified trichokirin.

EXAMPLE 2

S-Acetylmercaptosuccinoyl-Trichokirin and Mercaptosuccinoyl-Trichokirin 100 microliters of a solution of S-acetylmercaptosuccinic anhydride (SAMSA) containing 10.5 mg/ml (60.33 micromol/ml) in dimethylformamide are added to a solution of 5.8 mg of trichokirin (about 0.215 micromol) in 6 ml of 125 mM phosphate buffer, pH 7 (i.e. 0.973 mg/ml, about 0.036 micromol/ml). Incubation takes one hour, after which the reaction medium is purified by dialysis against 125 mM phosphate buffer, pH 7, to remove the excess reagent. This gives 5.7 ml of a solution of trichokirin S-acetylmercaptosuccinates containing 0.948 mg/ml. Reaction with hydroxylamine by ELLMAN's method (Methods in Enzymology 25, 457 (1972)) gives trichokirin mercaptosuccinate, or activated trichokirin, containing 0.7 free SH group per mol of trichokirin (spectrophotometric analysis). When examined by polyacrylamide gradient electrophoresis, this modified protein shows a single band with a molecular weight of the order of 28,000±3000, which is identical to that of the native protein.

EXAMPLE 3

Conjugate Obtained by Reacting the Antibody AT15E (Anti-Thy 1.2) with Mercaptosuccinoyl-Trichokirin A) Preparation of the modified antibody AT15E The antibody AT15E is a monoclonal antibody directed against the antigen Thy 1.2 of murine lymphocytes. This antibody is the one described in Journal of Immunology 122, 2491-8 (1979) and has been obtained from the hybridoma described in Hybridoma 1(1), 13-17 (1981).

25 microliters of a solution of N-succinimidin-3-yl 3-(pyridin-2-yldisulfanyl)propionate containing 5.5 mg/ml in ethanol are added to 3.7 ml of a solution of antibody AT15E containing 3.55 mg/ml (i.e. 0.087 micromol) in 0.1M borate buffer, pH 8.8.

Incubation takes 30 minutes and the excess reagent is then removed by dialysis against 125 mM phosphate buffer, pH 7. After dialysis, the protein solution is centrifuged to give 3.3 ml of a solution containing 3.4 mg/ml. By spectrophotometric analysis at 343 nm of the pyridine-2-thione released by exchange with 2-mercaptoethanol, it is found that the activated antibody obtained carries 3.2 mixed disulfide groups per mol of antibody.

B) Preparation of the immunotoxin (conjugate)

5 ml of the solution of modified trichokirin obtained above (i.e. 0.183 micromol) are added to 1.9 ml of the solution of activated antibody obtained above (i.e. 0.043 micromol) and the mixture is incubated for 20 hours at 25° C. in the presence of 350 microliters of a molar aqueous solution of hydroxylamine hydrochloride. The solution is centrifuged and then purified by filtration on a column of Sephadex G200, the optical density of the effluent being measured at 280 nm. Combination of the fractions containing both the antibody and the TK gives 20 ml of a solution of immunotoxin containing 0.215 mg/ml (i.e. 4.3 mg). This solution contains 0.045 mg/ml of modified trichokirin coupled to the antibody.

The average degree of coupling in this preparation is 1.5 TK per mol of antibody.

IMMUNOTOXIN ACTIVITY TESTS

One of the properties of trichokirin is to inhibit protein synthesis in eucaryotic cells. The tests performed are therefore tests for the inhibition of protein synthesis:

either on an acellular model or on a cell model.

A) The acellular model: inhibitory activity of the toxin

The in vitro protocol uses appropriately complemented subcellular fractions of rat liver capable of incorporating $^{14}C$-phenylalanine in the presence of an artificial messenger RNA: polyuridylic acid.

The procedure employed for preparing the subcellular fractions and measuring the incorporation of $^{14}C$-phenylalanine is an adaptation of the method described in BBA 312, 608-615 (1973), using both a microsomal fraction and a cytosol fraction of the rat hepatocytes. The sample containing the trichokirin is introduced in the form of a solution appropriately diluted in a 50 mM tris-HCl buffer, pH 7.6, containing 0.2% of 2-mercaptoethanol and 15 micrograms/ml of bovine serum albumin. The count data are used to calculate, relative to a reference medium without inhibitor, the percentage inhibition of the incorporation of $^{14}C$-phenylalanine for each reaction medium.

The values obtained together make it possible to determine the concentration of trichokirin (or $IC_{50}$) which inhibits the incorporation of $^{14}C$-phenylalanine by 50% under the experimental conditions. Thus, the $IC_{50}$ of native trichokirin was found to be equal to $7.10^{-11}$M, while that of the modified trichokirin was found to be equal to 8-$10.10^{-11}$ mol/liter. Therefore, the modification does not cause a significant loss of activity of the trichokirin.

B) Specific cytotoxicity of the trichokirin immunotoxin on a cell model

The biological activity of trichokirin is to inhibit protein synthesis in eucaryotic cell systems. The technique employed uses a cell model in which the effect of the substances studied on the incorporation of $^{14}C$-leucine into cancel cells in culture is measured. The cells used belong to the T2 cell line derived from a T murine leukemia expressing the surface antigen Thy 1.2. The cells are incubated in the presence of different concentrations of the substance to be studied, and then, when incubation has ended, the degree of incorporation of $^{14}C$-leucine by the cells treated in this way is measured.

This measurement is carried out by a technique adapted from the procedure described in Journal of Biological Chemistry 1974, 249(II), 3557-3562, using the tracer $^{14}C$-leucine to determine the degree of protein synthesis. The radioactivity incorporated is determined here on the whole cells isolated by filtration.

On the basis of these determinations, it is possible to draw the dose/effect curves, plotting, on the abscissa, the molar concentration of trichokirin in the substances studied, and, on the ordinate, the incorporation of $^{14}C$-leucine expressed as a percentage of the incorporation by control cells cultivated in the absence of any substance affecting protein synthesis.

It is thus possible to determine, for each substance studied, the concentration which causes a 50% inhibition of the incorporation of $^{14}C$-leucine, or "50% inhibitory concentration" ($IC_{50}$). Table 2 shows the $IC_{50}$ values obtained in the same experiment with the trichokirin immunotoxin on the one hand and uncoupled trichokirin on the other.

TABLE 2

| Product | 50% inhibitory concentration |
|---|---|
| Trichokirin IT | $2 \times 10^{-10}$ M |
| Trichokirin | $2 \times 10^{-6}$ M |

It can be seen that the trichokirin IT has a very strong cytotoxic activity which is more than 10,000 times higher than that of uncoupled trichokirin.

This novel class of immunotoxins can be used to treat cancerous or non-cancerous diseases where the target cells to be destroyed would be recognized by the antibody used to prepare the immunotoxin. The optimum modes of administration and the duration of the treatment will have to be determined in each case according to the subject and the nature of the disease to be treated.

The biologically active products of the invention can be formulated for administration by any suitable method. Usually, the active principle will be administered by injection and will be formulated in an apyrogenic sterile liquid, preferably water, which can contain physiologically acceptable salts, such as buffers or sodium chloride, so as to give an isotonic solution.

For an antitumoral treatment, the daily dose of trichokirin conjugated with an antibody is preferably between 1 and 100 mg and advantageously from 5 to 50 mg, for example about 10 mg.

The dosage units containing trichokirin in the form of a conjugate, for example ampoules for injection, will therefore usually contain from 1 to 100 mg of trichokirin conjugate.

What is claimed is:

1. Trichokirin mercaptosuccinates of the formula:

$$TK^{\circ}\!-\!(CO-\underset{\displaystyle CH_2COOH}{\underset{|}{CH}}-S-W)_n$$

in which TK° represents trichokirin, W represents hydrogen or the acetyl group and n can vary between 0.2 and 3.

2. Trichokirin mercaptosuccinates as claimed in claim 1, wherein n varies between 0.4 and 1.

3. Trichokirin mercaptosuccinates as claimed in claim 1, wherein W is hydrogen and n is 0.7.

4. Trichokirin mercaptosuccinates as claimed in claim 1, wherein W is acetyl and n is 0.7.

5. A process for the preparation of trichokirin mercaptosuccinates of formula:

$$TK^{\circ}(CO-\underset{\displaystyle CH_2COOH}{\underset{|}{CH}}-S-W)_n$$

in which TK° represents trichokirin, W represents hydrogen or the acetyl group and n can vary between 0.2 and 3, which process comprises reacting S-mercaptosuccinic anhydride with trichokirin.

* * * * *